(12) United States Patent
Lang

(10) Patent No.: US 6,840,932 B2
(45) Date of Patent: Jan. 11, 2005

(54) MEDICAL INSTRUMENT

(75) Inventor: Dieter Lang, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 419 days.

(21) Appl. No.: 10/103,088

(22) Filed: Mar. 21, 2002

(65) Prior Publication Data

US 2002/0143354 A1 Oct. 3, 2002

Related U.S. Application Data

(63) Continuation of application No. PCT/EP00/08814, filed on Sep. 9, 2000.

(30) Foreign Application Priority Data

Sep. 21, 1999 (DE) .......................... 199 45 228

(51) Int. Cl.⁷ ............................................... A61B 17/00
(52) U.S. Cl. ................ 606/1; 600/101; 606/2
(58) Field of Search .......................... 606/1–19, 39–52, 606/110–126, 167, 205–211, 107, 135, 138, 139; 600/101, 123, 133, 152, 153, 155, 159, 201–246; 604/19, 513, 164.08, 533, 534–539, 284, 288.03, 905

(56) References Cited

U.S. PATENT DOCUMENTS

| | | | |
|---|---|---|---|
| 2,691,370 A | 10/1954 | Wallace | 128/6 |
| 4,646,751 A | 3/1987 | Maslanka | 128/751 |
| 4,919,152 A | 4/1990 | Ger | 128/898 |
| 5,290,308 A | 3/1994 | Knight et al. | 606/205 |
| 5,344,428 A | 9/1994 | Griffiths | 606/205 |
| 5,489,290 A * | 2/1996 | Furnish | 606/170 |
| 5,569,284 A | 10/1996 | Young et al. | 606/180 |
| 5,569,298 A | 10/1996 | Schnell | 606/205 |
| 5,827,299 A * | 10/1998 | Thomason et al. | 606/148 |
| 5,928,255 A * | 7/1999 | Meade et al. | 606/170 |
| 6,315,774 B1 * | 11/2001 | Daniel et al. | 606/15 |
| 6,663,643 B2 * | 12/2003 | Field et al. | 606/144 |

FOREIGN PATENT DOCUMENTS

| | | |
|---|---|---|
| DE | 694 17 361 | 5/1994 |
| DE | 43 07 539 | 9/1994 |
| DE | 196 46 584 | 4/1998 |
| DE | 197 56 629 | 9/1998 |
| DE | 298 20 429 | 1/1999 |

\* cited by examiner

Primary Examiner—Glenn K. Dawson
(74) Attorney, Agent, or Firm—St. Onge Steward Johnston & Reens LLC

(57) ABSTRACT

The invention relates to a medical instrument with an elongated shaft (1) and with a handle part (2) that is linked with the proximal end of the shaft (1) and that is used to actuate a tool (4) located on the distal end of the shaft (1). Said shaft (1), in the area of the proximal end, is provided with a seakable flushing connection piece (5). Air and/or a flushing liquid can be guided through said flushing connection piece, especially for the purpose of cleaning, via an adjacent flushing channel (6) up to the stem of the shaft (1). The flushing connection piece (5) is disposed in an acute angle (alpha) with respect to the shaft (1) and faces the proximal end of the shaft (1). The aim of the invention is to provide a medical instrument that is easy to handle and that can be reliably cleaned via the flushing connection piece (5). To this end, the flushing channel (6) is configured as a direct straight and free extension of the flushing connection piece (5) and is also disposed in an acute angle (alpha) with respect to the shaft (1) and faces the proximal end of the shaft (1).

9 Claims, 4 Drawing Sheets

MEDICAL INSTRUMENT

This application is a continuation of pending International Application PCT/EP00/08814 filed on Sep. 9, 2000, which designates the United States and claims priority of German Application 19945228.8 filed on Sep. 21, 1999.

FIELD OF THE INVENTION

The invention relates to a medical instrument with an elongated shaft and with a handle part that is linked with the proximal end of the shaft and that is used to actuate a tool located on the distal end of the shaft. Said shaft, in the area of the proximal end, is provided with a sealable flushing connection piece. Air and/or a flushing liquid can be guided through said flushing connection piece, especially for the purpose of cleaning, via an adjacent flushing channel up to the stem of the shaft. The flushing connection piece is disposed in an acute angle with respect to the shaft and faces the proximal end of the shaft.

In medical instruments in common use, the flushing connection piece and flushing channel serve to cleanse the shaft of the instrument in the area of its stem on the handle part and the hollow cylindrical part of the shaft with air and/or flushing fluid. The shaft of most medical instruments is insulated at the proximal end to prevent penetration by unclean materials; therefore flushing fluid introduced by way of the flushing connection piece can flow out only through the distal end. The flushing connection pieces of well-known medical instruments are configured as Luer couplings heading perpendicularly away from the shaft, which can be closed off by means of separate sealing plugs. Besides the fact that the sealing plug can be misplaced, the configuration of the flushing connection piece as a perpendicularly extending Luer coupling can be a disadvantage, because it restricts the surgeon's view and/or the freedom of movement. The perpendicular injection of flushing fluid is also a disadvantage, because the proximal end of the shaft is not always sufficiently treated with flushing fluid as a result.

A medical instrument of this type is known from U.S. Pat. No. 5,290,308A. With this well-known medical instrument, the flushing connection piece is mounted on the shaft of the affixed knob in such a way that the knob is at an acute angle to the shaft and points toward the proximal end of the shaft. The flushing connection piece is open to the environment and on its lower end, located in the knob, is closed off by a spring-actuated ball valve. This ball valve closes the passage from the flushing connection piece to the actual flushing channel. Because the ball valve is so arranged that the entering flushing fluid must first counteract the spring tension in order to open the valve and thereby the entry to the flushing channel, large losses of pressure occur in the passage to the flushing channel, so that the flushing fluid enters the flushing channel almost void of pressure, a circumstance that again can significantly weaken the cleansing power. This loss of pressure in the well-known instrument is aggravated further by the fact that, from the arrangement of the ball vale, the flushing fluid must be diverted by 90 degrees on its way into the flushing channel.

As a result of this technological status, the aim of the invention is to provide a medical instrument of the aforementioned type that is refined in such a way that it is easy to handle and can be reliably cleaned via the flushing connection piece. To this end, the flushing channel is configured as a direct straight and free extension of the flushing connection piece and is also disposed in an acute angle with respect to the shaft and faces the proximal end of the shaft.

Through the inventive configuration of the flushing channel as a straight extension of the flushing connection piece, which in addition is free of built-in elements, such as valves, the flushing fluid, which can for instance be injected into the flushing connection piece by means of an injection, can reach the proximal end of the shaft unhindered and thus without loss of pressure. Through this pressure impulse, firmly seated deposits may also be reliably removed. The flushing connection piece, diagonally disposed with respect to the proximal end of the shaft, along with the flushing channel thus results in improved cleansing of the proximal end of the shaft, because the flushing fluid is aimed and introduced directly onto this end.

In addition, it is proposed with this invention that the flushing connection piece can be closed off by means of a sealing element firmly secured to the shaft. The advantage of this inventive configuration is that there is no longer any risk that the sealing element can become lost.

In a particularly advantage embodiment of the invention, the sealing element is configured as a housing coaxially attached onto the shaft with a locking arm that basically points radially away from the housing, and that the housing can be rotated around the longitudinal axis of the shaft. The coaxial arrangement of the housing of the sealing element on the shaft further ensures that the medical instrument remains slender and compact in structure.

To ensure good sealing of the flushing connection piece by means of the sealing element, it is proposed, in a practical embodiment of the invention, that the sealing element is pre-tensioned in the direction toward the proximal end of the shaft and thus in the direction toward the flushing connection piece.

To produce this tensioning of the sealing element, it is proposed that a pressure spring or a pressure rubber ring is arranged within the housing on the shaft. By means of this pressure spring, arranged for instance coaxially on the shaft, the sealing element is permanently pressured in the direction toward the flushing connection piece, and as a result a secure sealing of the flushing connection piece is ensured in the closed position of the sealing element.

The sealing of the flushing connection piece by means of the sealing arm can be improved if an insulating element is arranged on the side of the sealing arm toward the flushing connection piece. The insulating element should preferably be configured as a plug that is insertable in a bore hole in the sealing arm and can easily be replaced on becoming worn.

A final proposal of the invention is that the shaft is secured removably on the handle part. Because of the configuration of the flushing connection piece on the proximal end of the shaft, it is possible to equip the medical instrument both with a shaft that is permanently connected to the handle part and with a removable shaft, without any negative effect on the flushing by means of the flushing connection piece.

BRIEF DESCRIPTION OF THE DRAWINGS

Additional characteristics and advantages of the invention can be seen in the ensuing description of the related illustrations, in which a model of an inventive medical instrument is depicted as an example. The illustrations are as follows.

DETAILED DESCRIPTION OF THE DRAWINGS

Figure 1:
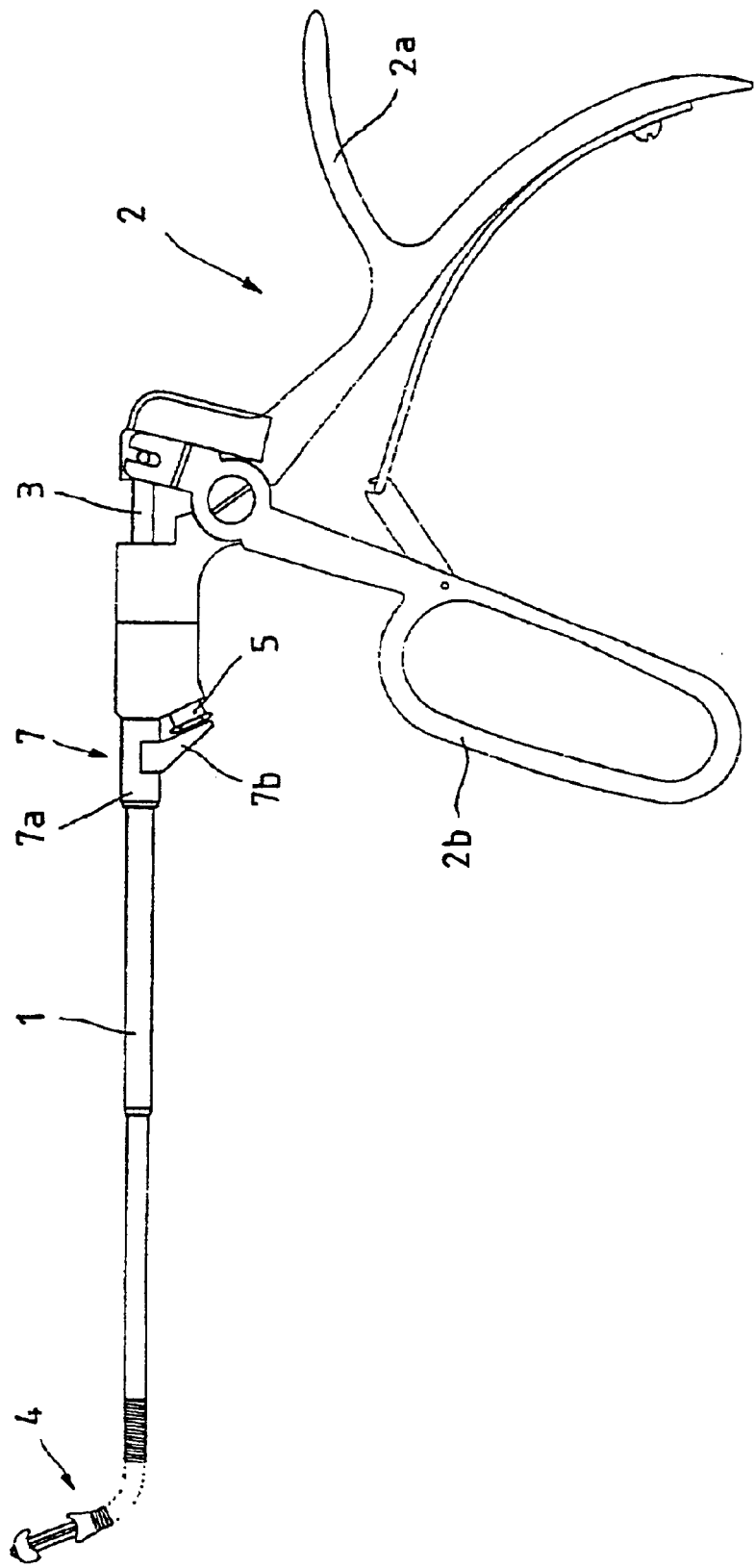
FIG. 1 Lateral view of an inventive medical instrument

FIG. 1 shows a medical instrument with an elongated shaft 1, and with a handle part 2 that is linked with the proximal end of the shaft 1 with a rigid gripping part 2a and with a gripping part 2b that can rotate with respect to the rigid gripping part 2a. A tool 4 on the distal end of the shaft 1 can be actuated by means of a handle 2 by a push-pull rod 3 stored in the shaft 1. The pictured model is an HNO instrument.

For cleaning the illustrated medical instrument and particularly the stem of the shaft 1 on the handle 2 as well as of the stem of the hollow cylindrical part of the shaft 1 that serves for storing the push-pull rod 3, a flushing connection piece 5 is installed in the area of the proximal end of the shaft 1. Air and/or flushing fluid can be introduced into the medical instrument by means of this flushing connection piece. The flushing fluid reaches the proximal end of the shaft 1 by means of a flushing channel 6, as can be seen in the model in FIG. 3.

Figure 3:
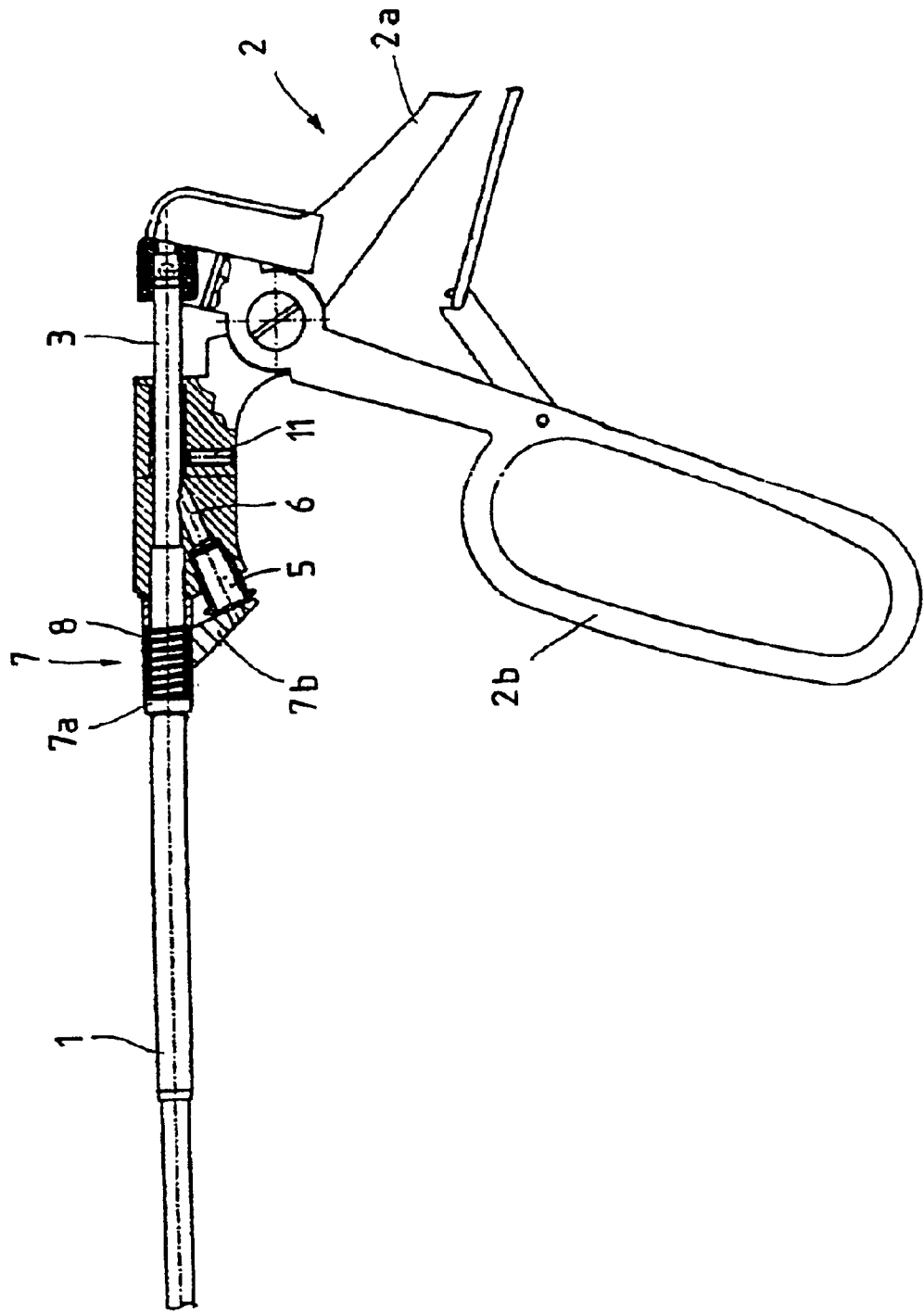
FIG. 3 Partially cut-out lateral view of the medical instrument in accordance with FIG. 1
Figure 4:
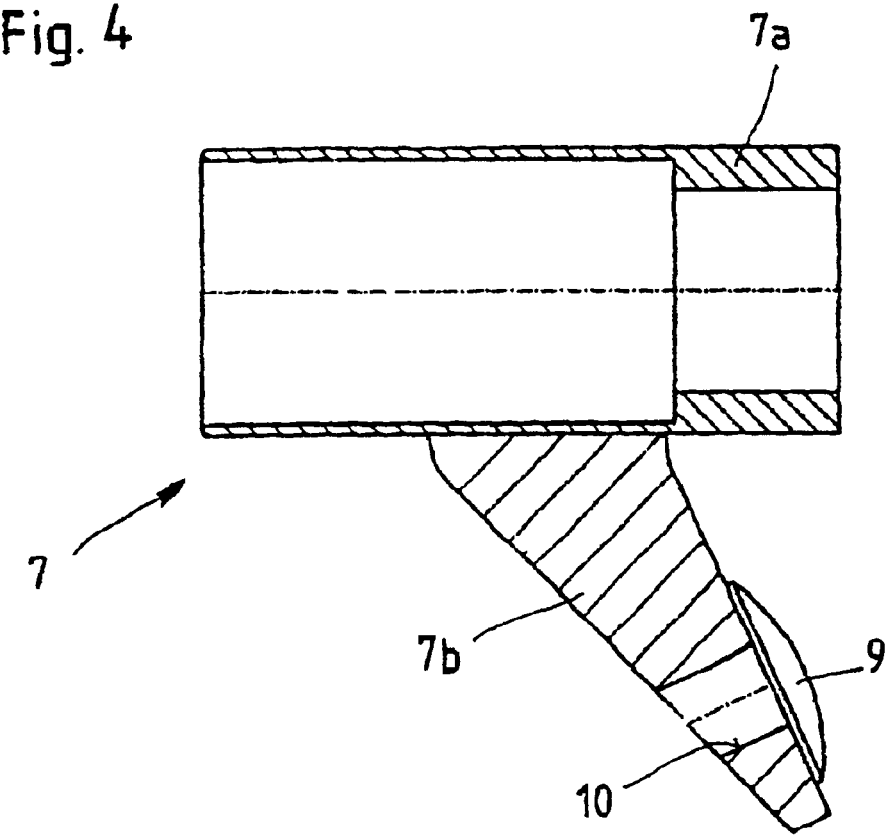
FIG. 4 Longitudinal section through the sealing element of the inventive medical instrument FIG. 5 Longitudinal section through the proximal end of the shaft of an inventive medical instrument
Figure 5:
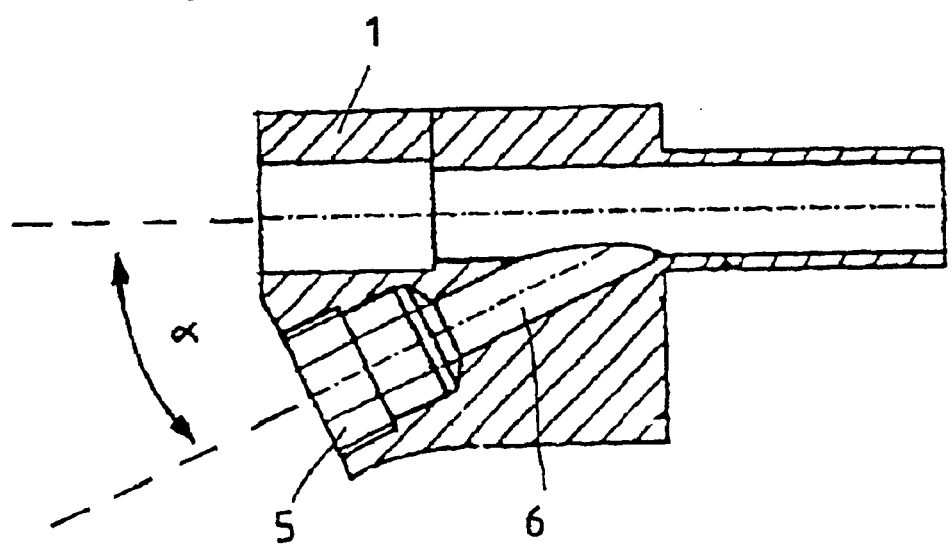

As can be seen in FIGS. 3 and 5, the flushing connection piece 5 and the flushing channel 6 are arranged at an acute angle alpha to the shaft 1, on the one hand in order to allow for an especially slender, compact structure of the medical instrument and on the other hand to allow for perfect cleaning of the proximal end of the shaft 1. Because the proximal end of the shaft tends to be insulated to avoid penetration of dirt, the flushing fluid that is introduced can drain out only by way of the distal end of the shaft 1. As a result, it is particularly advantageous if the flushing fluid to be introduced is guided directly onto the insulated proximal end of the shaft.

Figure 2:
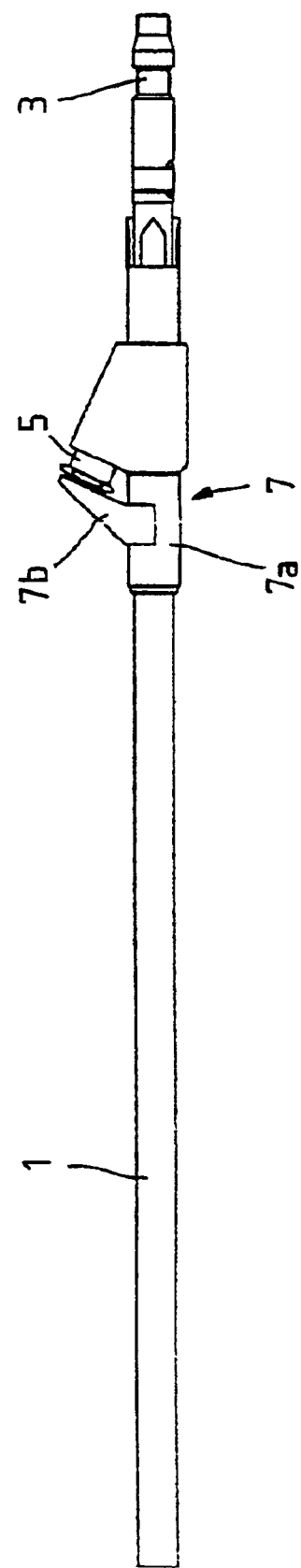
FIG. 2 Lateral view of a removable shaft with an inventive flushing connection

As can also be seen from FIGS. 1 to 3, the flushing connection piece 5 can be sealed off by means of a sealing element 7. In the illustrated model, the sealing element 7 consists of a housing 7a coaxially arranged on the shaft 1 with a sealing arm 7b that is basically directed radially away from the housing 7a. The sealing element 7 can be rotated freely around the longitudinal axis of the shaft 1. The fixed storage of the sealing element 7 on the shaft 1 has the advantage that the sealing element 7 cannot become lost.

In order to press the sealing element 7 tight enough for insulation against the flushing connection piece 5, the sealing element 7 is pre-tensioned in the direction toward the proximal end of the shaft 1. For this purpose, as shown in illustrated model, a pressure spring 8 is arranged coaxially on the shaft 1 within the housing 7a. It is also possible, of course, to provide this pre-tensioning by means of a pressure rubber ring for instance.

In the sealed position of the sealing element 7, as seen in FIGS. 1 to 3, the sealing arm 7b configured on the housing 7a insulates the flushing connection piece 5. This insulation is improved if an insulating element 9 is arranged on the side of the sealing arm 7b turned toward the flushing connection piece 5. This insulating element 9 in the illustrated model in a bore hole 10 of the sealing arm 7b is intended to ensure that no foreign materials reach the connecting area of the shaft 1 by way of the flushing connection piece 5 and the flushing channel 6.

The sealing element 7 is actuated as follows.

Starting from the closed position depicted in FIGS. 1 to 3, in order to clean the medical instrument, first the flushing connection piece 5 must be opened. For this purpose the housing 7a must be pushed against the counterforce of the pressure spring 8 all the way to the distal end of the shaft 1, in order to remove the insulating element 9 from the insulating position on the flushing connection piece 5. Simultaneously with the axial moving of the sealing element 7 up to the distal end of the shaft 1, the housing also can now be turned around the longitudinal axis of he shaft 1 so that the sealing arm 7b no longer lies in front of the flushing connection piece 5.

Air and/or flushing fluid for purposes of cleaning can now be introduced by means of the flushing connection piece 5 and the flushing channel 6. Flushing fluid, for instance, can be introduced by means of an injection into the flushing connection piece 5. The flushing fluid flows out again from the distal end of the shaft 1.

Upon completion of the flushing operation, the housing 7a is again pressed against the counterforce of the pressure spring 8 all the way to the distal end of the shaft 1 and simultaneously it is wound around the longitudinal axis of the shaft 1 until the sealing arm 7b in closed position again presses the insulating element 9 tightly against the flushing connection piece 5.

In the illustrated model of a medical instrument, the shaft 1 is connected removably with the handle 2, as especially demonstrated in FIG. 3. The shaft 1 is secured on the handle 2 by means of a securing element 11, for instance a screw. In addition to this embodiment it is also possible to connect the shaft 1 with the handle 2 with a rapid coupling system in accordance with DE 43 07 539 A1, as shown in FIG. 2.

On the whole, a medical instrument designed in this manner is distinguished by its compact and slender structure as well as good cleanability. The slender structure allows the operator, especially while operating in direct view, that is without additional assistance of an endoscope, a good overview of the operating area along with simultaneous freedom of movement.

Reference Key

1. Shaft
2. Handle
2a. Rigid grip part
2b. Rotatable grip part
3. Push-pull rod
4. Tool
5. Flushing connection piece
6. Flushing channel
7. Sealing element
7a. Housing
7b. Sealing arm
8. Pressure spring
9. Insulating element
10. Bore hole
11. Securing element alpha Angle

What is claimed is:

1. Medical instrument with an elongated shaft and with a handle part that is linked with the proximal end of the shaft and that is used to actuate a tool located on the distal end of the shaft, where said shaft, in the area of the proximal end, is provided with a sealable flushing connection piece through which air and/or a flushing liquid can be guided via an adjacent flushing channel up to a stem of the shaft and the flushing connection piece is disposed in an acute angle with respect to the shaft and faces the proximal end of the shaft distinguished in that the flushing channel is configured as a direct straight and free extension of the flushing connection piece and is also disposed at an acute angle with respect to the shaft and faces the proximal end of the shaft.

2. Medical instrument in accordance with claim 1, distinguished in that the flushing connection piece is sealable by means of a sealing element secured on the shaft.

3. Medical instrument in accordance with claim 2, distinguished in that the sealing element is configured as a housing arranged coaxially on the shaft with a sealing arm pointing generally radially away from the housing, where the housing can be rotated around the longitudinal axis of the shaft.

4. Medical instrument in accordance with claim 3, distinguished in that an insulating element is arranged on the side of the sealing arm facing the flushing connection piece.

5. Medical instrument in accordance with claim 4, distinguished in that the insulating element is configured as a plug that can be installed into a bore hole in the sealing arm.

6. Medical instrument in accordance with claim 2, distinguished in that the sealing element is pre-tensioned in the direction toward the proximal end of the shaft.

7. Medical instrument in accordance with claim 6, distinguished in that a pressure spring is arranged coaxially on the shaft inside the housing to produce the pre-tensioning.

8. Medical instrument in accordance with claim 6, distinguished in that a pressure rubber ring is arranged coaxially on the shaft inside the housing to produce the pre-tensioning.

9. Medical insturment in accordance with claim 1, distinguished ini that the shaft can be secured removably on the handle piece.

\* \* \* \* \*